(12) United States Patent
Farhadiroushan et al.

(10) Patent No.: US 9,651,474 B2
(45) Date of Patent: May 16, 2017

(54) FIBRE OPTIC MONITORING INSTALLATION AND METHOD

(75) Inventors: Mahmoud Farhadiroushan, London (GB); Mladen Todorov, Welling (GB)

(73) Assignee: Silixa Ltd., Hertfordshire (GB)

(*) Notice: Subject to any disclaimer, the term of this patent is extended or adjusted under 35 U.S.C. 154(b) by 428 days.

(21) Appl. No.: 13/884,235

(22) PCT Filed: Nov. 8, 2011

(86) PCT No.: PCT/GB2011/052176
§ 371 (c)(1),
(2), (4) Date: Oct. 29, 2013

(87) PCT Pub. No.: WO2012/063062
PCT Pub. Date: May 18, 2012

(65) Prior Publication Data
US 2014/0036957 A1    Feb. 6, 2014

(30) Foreign Application Priority Data
Nov. 8, 2010    (GB) .................................. 1018802.7

(51) Int. Cl.
*G01J 5/08* (2006.01)
*G01N 21/01* (2006.01)
(Continued)

(52) U.S. Cl.
CPC ............. *G01N 21/01* (2013.01); *G01K 1/14* (2013.01); *G01K 11/32* (2013.01); *G01M 11/086* (2013.01); *Y10T 29/49826* (2015.01)

(58) Field of Classification Search
CPC .......... G01K 11/32; G01N 2021/6484; G01N 2201/08; G01N 2201/1211; G01J 5/0826; G01J 5/08
(Continued)

(56) References Cited

U.S. PATENT DOCUMENTS 4,464,413 A * 8/1984 Murphy et al. .................. 427/6
4,812,645 A * 3/1989 Griffiths .................. 250/227.14
(Continued)

FOREIGN PATENT DOCUMENTS

FR    2688584 A1    9/1993
GB    2239310 A    6/1991
(Continued)

OTHER PUBLICATIONS

Combined Search and Examination Report from GB1018802.7 issued on Nov. 8, 2011 (6 pages).
(Continued)

*Primary Examiner* — Gail Kaplan Verbitsky
(74) *Attorney, Agent, or Firm* — Osha Liang LLP (57) ABSTRACT

The invention relates to installations for fiber optic monitoring of articles, and apparatus and methods for forming such installations, including a modular system and components for forming a fiber optic monitoring installation. Applications of the invention include the monitoring of vessels, chambers, and fluid conduits in industrial processing plants, and the invention has particular application to monitoring large vessels, for example temperature monitoring of vessels used in catalytic reforming processes. Convenient installation on or removal from the article being monitored is achieved by providing a support structure for the fiber optic length, which presents the fiber optic length in a preconfigured orientation suitable for monitoring the article. In a particular embodiment of the invention, the fiber optic length is disposed on a panel in a plurality of dense spiral patterns.

5 Claims, 9 Drawing Sheets

(51) Int. Cl.
*G01K 1/14* (2006.01)
*G01K 11/32* (2006.01)
*G01M 11/08* (2006.01)

(58) Field of Classification Search
USPC ... 374/120, 121, 141, 131, 161, 46, 45, 208, 374/130, 100, 112, 137; 356/43, 44; 385/12; 73/866.5
See application file for complete search history.

(56) References Cited

U.S. PATENT DOCUMENTS

| | | | | |
|---|---|---|---|---|
| 5,356,220 | A * | 10/1994 | Iida | C21B 7/24 374/124 |
| 5,594,819 | A * | 1/1997 | Narendran | G01B 11/18 250/227.14 |
| 5,740,291 | A * | 4/1998 | De Lasa et al. | 385/31 |
| 5,821,861 | A * | 10/1998 | Hartog | G01K 11/32 250/227.18 |
| 6,079,875 | A * | 6/2000 | Klass et al. | 374/130 |
| 6,644,848 | B1 * | 11/2003 | Clayton | E21B 17/01 250/227.14 |
| 6,813,403 | B2 * | 11/2004 | Tennyson | 385/12 |
| 7,399,446 | B2 * | 7/2008 | Herzog | G01K 11/32 374/E11.015 |
| 7,534,031 | B2 * | 5/2009 | Yamamoto | G01K 11/32 356/32 |
| 2004/0037752 | A1 | 2/2004 | Herzog | |
| 2006/0133450 | A1 * | 6/2006 | Shioji | G01K 11/32 374/161 |
| 2006/0225507 | A1 * | 10/2006 | Paulson | F17D 5/02 73/592 |
| 2006/0251147 | A1 * | 11/2006 | Balan | G01K 11/3213 374/152 |
| 2007/0009007 | A1 * | 1/2007 | Nicholls | G01K 11/32 374/10 |
| 2008/0121171 | A1 * | 5/2008 | Hulsey | G01K 11/12 116/216 |
| 2009/0123110 | A1 * | 5/2009 | Park et al. | 385/13 |
| 2009/0279583 | A1 * | 11/2009 | Hampson et al. | 374/131 |
| 2010/0011865 | A1 | 1/2010 | Saxena et al. | |
| 2016/0220131 | A1 * | 8/2016 | Kishida | A61B 5/0215 |
| 2016/0258743 | A1 * | 9/2016 | Yao | G01B 11/161 |

FOREIGN PATENT DOCUMENTS

| | | |
|---|---|---|
| JP | 4216425 A | 8/1992 |
| JP | 2003065730 A * | 3/2003 |
| WO | 96/10735 A1 | 4/1996 |
| WO | 97/15805 A1 | 5/1997 |
| WO | 2009061323 A1 | 5/2009 |

OTHER PUBLICATIONS

International Search Report issued in corresponding International Application No. PCT/GB2011/052176; Dated Feb. 19, 2014 (6 pages).

* cited by examiner

FIBRE OPTIC MONITORING INSTALLATION AND METHOD

The invention relates to installations for fibre optic monitoring of articles, and apparatus and methods for forming such installations. Aspects of the invention relate to a modular system for forming a fibre optic monitoring installation and components thereof. Applications of the invention include the monitoring of vessels, chambers, and fluid conduits in industrial processing plants, and the invention has particular application to monitoring large vessels. Particular of the invention are concerned with the temperature monitoring of vessels used in catalytic reforming processes.

BACKGROUND TO THE INVENTION

The background to the invention will be described in the context of catalytic reforming processes, although the invention is not so limited and has application to a variety of industrial processes in which monitoring of plant equipment, including vessels, chambers and fluid conduits, is beneficial. It will be apparent that the invention is particularly useful in industrial applications which use large vessels or chambers for containing fluids and/or feedstocks during reaction processes.

Figure 1:
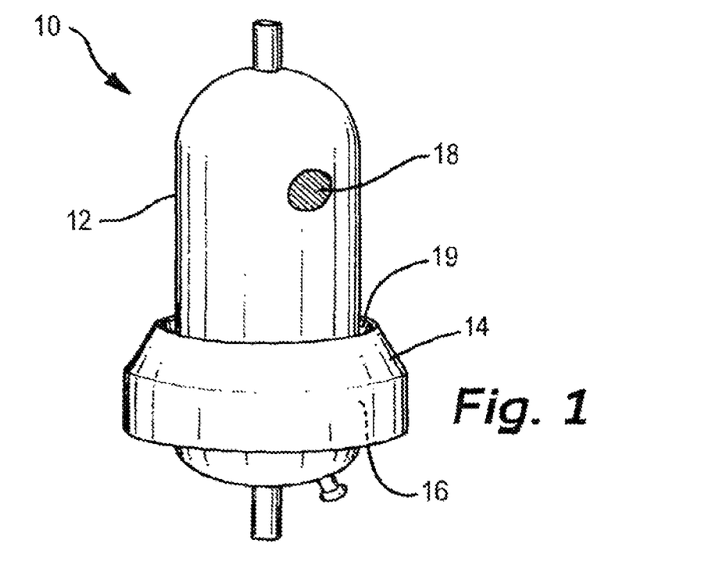
FIG. 1 is a perspective view of a typical vessel used in a catalytic reforming process.

Catalytic reforming processes are used to increase the octane ratings of petroleum refinery feedstocks to form into high octane liquid products, and are utilised during the generation of the majority of the world's gasoline. A number of catalytic reforming processes have been development since 1940s, all of which use platinum and/or rhenium catalysts. Examples include the proprietary Platforming process developed by Universal Oil Products; the Rheniforming process proprietary to Chevron Oil Company; the Powerforming process proprietary to ExxonMobil; and the proprietary Ultraforming process of BP. A typical catalytic reforming process takes place in a large cylindrical vessel of approximately 2 to 4 meters in diameter, and is a continuous process which takes place at a temperature of around 400° C. to 600° C. FIG. 1 shows a typical vessel 10, having a cylindrical outer wall 12, oriented vertically on a concrete support 14 which surrounds a lower part 16 of the vessel.

In order to prevent heat losses and to preserve the external wall of the vessel 10, a stainless steel liner is fitted on the interior wall of the vessel, with a layer of insulating material between the inner and outer walls. During normal operation, the typical temperature of the outer wall is around 180° C. Over its lifetime, the interior stainless steel liner can be damaged, which may allow leakage of the hot reactants into the insulation layer. This exposes the outer wall to high temperatures, and the inside surface of the outer wall to hydrogen. "Hot spots" develop on the vessel surface. In the presence of the hot spot, High Temperature Hydrogen Attack (HTHA) can lead to severe local weakening of the structure. Conventionally, hot spots have been detected through a change in colour of heat-sensitive paint applied to the outer surface of the vessel. Typically, this will change colour at temperatures above 200° C. and provide a visual indication 18 of a hot spot.

For many industrial installations, visual inspection by the use of heat sensitive paints is inadequate for the monitoring of the condition of the vessel. Firstly, the heat sensitive paint does not provide any quantitative data about the maximum temperature that has been reached. Secondly, the geometry of the installation in the vessel often means that visual inspection is not possible. For example, many catalytic reforming process vessels have a concrete support which obscures visual inspection of the vessel, of the type shown in FIG. 1.

More recently, it has been proposed to provide temperature monitoring of catalytic reforming process vessels by using fibre optic Distributed Temperature Sensor (DTS) systems. An example of a distributed temperature sensor is described in GB 2239310. Another example of a suitable DTS system is the applicant's proprietary system marketed under the ULTIMA trade mark.

In a typical application of a fibre optic monitoring system, the fibre optic is wrapped around the outer surface of a vessel in a continuous length, to provide a suitable surface distribution for monitoring the temperature of the vessel. However, to date this approach has been limited to the exposed parts of the vessel; the surface of the vessel which is beneath structural elements such as the concrete support 14 is unable to be monitored due to installation difficulties.

Other disadvantages of the previously proposed systems are apparent. In particular, installing the fibre optic on the surface of the vessel by the conventional methods can only be performed during process shutdowns. The installation method is also time consuming and labour intensive. Conventional installation methods also have an unacceptable risk of mechanical damage to the cable. Furthermore, this type of installation is not well disposed to removal and replacement, which may be necessary to allow inspection and repair of the vessel, or to replace a malfunctioning or damaged fibre optic length.

It is amongst the aims and objects of the invention to provide a fibre optic monitoring installation, apparatus and/or method which overcomes one or more drawbacks and deficiencies of the presently available apparatus and methods.

Additional aims and objects of the invention will become apparent from the following description.

SUMMARY OF THE INVENTION

According to a first aspect of the invention, there is provided a fibre optic monitoring installation comprising:
an article having an outer surface to be monitored;
a fibre optic support structure arranged to support a fibre optic length in a predetermined orientation which corresponds to a part of a surface of an article to be monitored;
means for locating the fibre optic support structure in relation to article such that, in use, the fibre optic length is sensitive to a condition of the surface of the article; and
fibre optic instrumentation coupled to the fibre optic length.

A predetermined orientation shall be taken to include an orientation, arrangement, configuration and/or pattern by which the fibre optic length is capable of facilitating measurement of a condition of the surface of the article such as, for example, described in relation to the preferred embodiments.

By providing a support structure for the fibre optic length, the fibre optic length may be attached to the support structure in a preconfigured orientation suitable for monitoring the article. This enables convenient installation on or removal from the article. The fibre optic length is preferably attached to the support structure before the support structure is located in relation to the article to be monitored. However, in another embodiment the support structure may be configured to be located in relation to the article to form an in situ support for subsequent installation of the fibre optic length.

The support structure may define a monitoring area, which may correspond to a part of the article, and the fibre optic length may be arranged in a preconfigured pattern or orientation over the area defined by the support structure.

Preferably, the installation comprises at least one module, the module comprising the fibre optic support structure, and a fibre optic length supported by the support structure in a predetermined orientation corresponding to a part of a surface of the article. The support structure may for example be a preformed conduit or channel for receiving a fibre optic length, or may be a sleeve. The support structure may be a mesh panel. However, in one preferred embodiment, the support structure is a frame.

In another preferred embodiment, the support structure is a panel, in which case preferably the panel comprises a plurality of guide portions on a surface thereof to arrange the fibre optic length in the predetermined orientation. Preferably, the guide portions are arranged to arrange the fibre optic length in a plurality of fibre spiral patterns. Preferably, the panel comprises a plurality of apertures to allow the fibre to pass to another surface of the panel, for example between successive fibre spiral patterns. Preferably, the panel further comprises attachment means to hold the fibre optic length in the predetermined orientation.

Where support structure may be configured to be installed on the article to be monitored, and to subsequently receive the fibre optic length in situ on the article. The support structure may be configured as a sleeve or helical structure on the article.

The support structure may be configured to be installed on the article to be monitored, and to subsequently receive the fibre optic length in situ on the article.

Preferably the installation comprises a plurality of modules, each module comprising a fibre optic support structure and a fibre optic length. The installation may comprise means for locating the plurality of modules such that the fibre optic lengths are presented to the surface of the article. The invention may therefore provide a modular system, which facilitates installation at or on an article to be monitored. The shape and form of the modules, the number of modules and the manner in which they are arranged at or on the article, may be selected according to the type and shape of the article. Each module may therefore monitor a zone or area of the article.

In one embodiment, the installation comprises a plurality of modules of substantially the same shape and/or as one another. Therefore the modules may be interchangeable. Each module may correspond to a part of the shape of the article. For example, the article may be cylindrical, and the modules may be part-cylindrical such that together they form a substantially cylindrical shape.

The article may be a part of an industrial process facility, and may comprise a chamber or fluid conduit. In preferred embodiments of the invention, the article is a vessel, and it may have a substantially cylindrical outer surface. The invention has particular benefits for monitoring large articles. Where the article is a vessel, it may have a diameter greater than 1 meter, and may for example have a diameter in the range of 1 meter to 10 meters. The invention is particularly suitable for vessels having a diameter in the range of 2 to 4 meters, such as those used in catalytic reforming processes in the petroleum industry and in a particular embodiment, the vessel is a catalytic reforming process vessel. However, it will be appreciated that the principles of the invention can be applied to vessels of other shapes and sizes.

The installation preferably comprises a fibre optic loop coupled to the fibre optic instrumentation, and one or more fibre optic lengths coupled to the fibre optic loops. Preferably, a plurality of fibre optic lengths is coupled to fibre optic instrumentation, and most preferably at least two of the plurality of fibre optic lengths is connected in series in a fibre optic circuit.

Preferably, the fibre optic instrumentation is coupled to the loop at both ends of the loop. This permits operation of system even if a part of the fibre optic becomes broken. In addition, it enables individual lengths to be removed from the installation without affecting the operation of the remaining modules. This enables modules to be replaced and/or repaired, and also allows a module to be removed for visual inspection of the article while fibre optic monitoring continues to take place via other modules (which remain connected to the fibre optic instrumentation).

The installation may comprise means for connecting one or more of the plurality of modules together. At least one module may comprise a connector for connecting to an adjacent module. The connector may form a part of the module, and preferably forms a part of the frame.

In a preferred embodiment, the installation comprises means for tensioning the support structure against the article to be monitored. The installation may comprise a plurality of modules tensioned together to locate the modules at or on the article.

The installation may comprise a mechanism for clamping the modules. The modules may be clamped to one another and/or maybe clamped to the article. Preferably, the installation comprises one or more clamping assemblies configured to locate the plurality of modules such that their respective fibre optic lengths are presented to the surface of the articles.

In one embodiment, the clamping assembly comprises a pivoting clamp assembly, configured to engage with formations on frames of the modules. The pivoting clamp assembly is preferably operable to engage with formations on the frame to bring adjacent frames together, and/or to impart tension to the installation.

The fibre optic monitoring instrumentation may be a distributed temperature sensor (DTS) instrument. Alternatively or in addition, the fibre optic instrumentation may comprise an acoustic monitoring sensor instrument, and/or a strain or pressure monitoring sensor instrument.

According to a second aspect of the invention, there is provided a method of forming a fibre optic monitoring installation, the method comprising:
providing a fibre optic length in a preconfigured orientation corresponding to at least a part of a surface of an article to be monitored;
presenting the preconfigured orientation of the fibre optic length to the surface of the article; and
coupling the fibre optic length to fibre optic monitoring instrumentation.

The fibre optic length may form part of a first module, the first module comprising a first frame, wherein the fibre optic length is supported by the frame.

Preferably, the method comprises the steps of providing a fibre optic support structure, and arranging the fibre optic length on the support structure in a predetermined orientation which corresponds to a part of a surface of the article. In a preferred embodiment, the method comprises arranging the fibre optic length on the support structure prior to its presentation to the surface of the article. However, in embodiments of the invention the method may comprise the steps of providing a support structure on the article and subsequently attaching the fibre optic length to the support structure. The method may include arranging the fibre optic length on the support structure so as to form a plurality of fibre spiral patterns.

The method may comprise the step of clamping the support structure and fibre optic length against the article. The method may comprise tensioning the support structure and/or fibre optic length against the article.

Embodiments of the second aspect of the invention may include one or more features of the first aspect of the invention or its embodiments, or vice versa.

It will be appreciated that the invention extends to constituent parts which are used in the above-described installation and methods. Therefore according to a third aspect of the invention, there is provided a kit of parts which, when assembled, forms a fibre optic monitoring installation, the kit of parts comprising:

a plurality of fibre optic support structures, each support structure configured to support a fibre optic length in an orientation corresponding to a part of a surface of an article to be monitored;

a plurality of fibre optic lengths, each configured to be supported on one of the plurality of frames, and configured to coupled to fibre optic monitoring instrumentation.

The kit of parts may further comprise fibre optic monitoring instrumentation, which may be a distributed temperature sensor instrument.

Embodiments of the third aspect of the invention may include one or more features of the first or second aspects of the invention or its embodiments, or vice versa.

According to a fourth aspect of the invention, there is provided a module for a fibre optic monitoring installation, the module comprising:

a first fibre optic length operable to be coupled to fibre optic monitoring instrumentation;

a first support structure configured to support the first fibre optic length in an orientation corresponding to at least a part of a surface of an article to be monitored;

means for locating the first support structure such that the first length of fibre optic is presented to the surface of the article.

Preferably, the module is configured to be attached to second and/or further modules, to together form a fibre optic monitoring installation. One or more of the second and/or further modules may comprise a fibre optic length operable to be coupled to fibre optic monitoring instrumentation; a frame configured to support the fibre optic length in an orientation corresponding to at least a part of a surface of the article to be monitored; means for locating the support structure such that the length of fibre optic is presented to the surface of the article.

Embodiments of the fourth aspect of the invention may include one or more features of any of the first to third aspects of the invention or its embodiments, or vice versa.

According to a fifth aspect of the invention, there is provided an apparatus for a fibre optic monitoring installation, the apparatus comprising:

a frame configured to support a fibre optic length in an orientation corresponding to at least a part of a surface of an article to be monitored;

means for locating the frame such that a supported fibre optic is presented to the surface of the article.

Embodiments of the fifth aspect of the invention may include one or more features of any of the first to fourth aspects of the invention or its embodiments, or vice versa.

According to a sixth aspect of the invention, there is provided a method of monitoring the temperature of a catalytic reforming process vessel, the method comprising:

providing a fibre optic monitoring installation on the vessel, the installation comprising a plurality of modules each having a support structure and a fibre optic length supported by the support structure in an orientation corresponding to a part of an outer surface of the vessel;

propagating light in at least one of the fibre optic lengths; and collecting data from the fibre optic monitoring installation at a distributed temperature sensor receiver.

The method may comprise processing the collected data to provide a distributed temperature map of the vessel.

Preferably, the method comprises generating a signal in response to the detection of an undesirable temperature condition of the vessel. The signal may comprise a visual and/or audible warning signal.

The method may comprise recording a time series of the collected data.

Preferably, the method comprises collecting data from one or more fibre spiral patterns of the fibre optic length and processing the data as if received from a corresponding number of point sensors.

Embodiments of the sixth aspect of the invention may include one or more features of any of the first to fifth aspects of the invention or its embodiments, or vice versa.

According to a seventh aspect of the invention, there is provided a method of forming a fibre optic monitoring installation, the method comprising:

providing a fibre optic support structure in a preconfigured shape corresponding to at least a part of a surface of an article to be monitored;

attaching a fibre optic length to the fibre optic support structure such that that the fibre optic length is in an orientation corresponding to at least a part of a surface of an article to be monitored;

locating the combined fibre optic length and support structure at the article to be monitored such that in use, the fibre optic length is sensitive to a condition of the to the surface of the article; and coupling the fibre optic length to fibre optic monitoring instrumentation.

Embodiments of the seventh aspect of the invention may include one or more features of any of the first to sixth aspects of the invention or its embodiments, or vice versa.

BRIEF DESCRIPTION OF THE DRAWINGS

There will now be described, by way of example only, various embodiments of the invention with reference to the drawings, of which.

DETAILED DESCRIPTION OF PREFERRED EMBODIMENTS

Referring firstly to FIG. 1, there is shown generally depicted at 10 a catalytic reforming process vessel having a cylindrical outer wall 12. The vessel 10 is oriented vertically on a concrete support 14 which surrounds a lower part 16 of the vessel. An annular space 19 of a few centimeters (3 to 10 cm) is provided between the concrete support 14 and the outer wall 12. However, the concrete support 14 prevents visual assessment of the vessel, and restricts manual access to the lower part 16 of the vessel.

Figure 2:
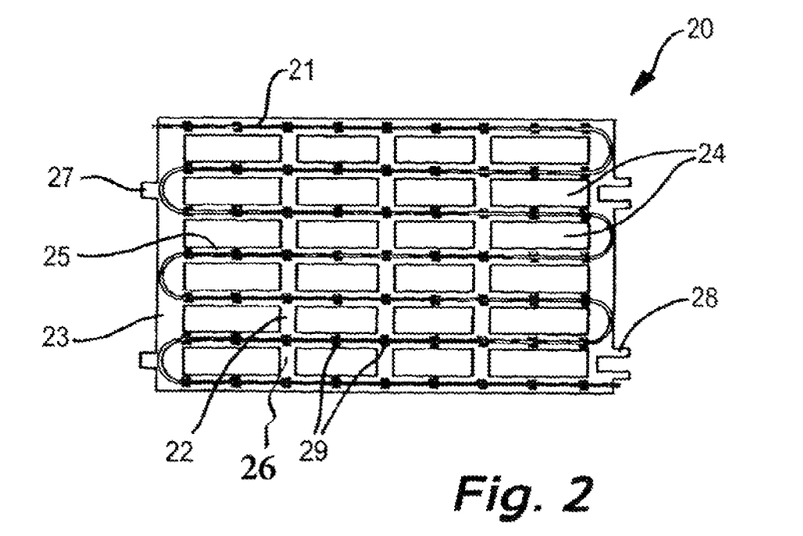
FIG. 2 is a side view of a module according to an embodiment of the invention.

FIG. 2 shows generally at 20 a module forming a part of a first embodiment of the invention. The module 20 is suitable for use as a component of a fibre optic monitoring system for the vessel 10. This embodiment of the invention is suitable for a wide range of industrial applications, and includes benefits in installation, removal, and monitoring inaccessible surfaces of the vessel.

The module 20 comprises a fibre optic length 21 supported by and attached to a support structure in the form of frame 22. The frame 22 is formed from a panel 23 of a thermally conductive metal material (for example stainless steel, aluminium or an alloy thereof). The panel 23 has preformed windows 24 between horizontal and vertical members 25, 26. Edges of the frame 22 comprise corresponding attachment features 27, 28 which are configured to attach the module 20 to an adjacent module (not shown) or other attachment feature of the installation. The fibre optic length 21 is attached to the frame 22 by attachment points 29 spaced along the frame, and follows a convoluted path over the areal extent of the frame to define a monitoring area. It will be appreciated that the pattern followed by the fibre optic length 21 can be varied according to the application (such as in the alternative embodiment shown in FIG. 11 and described in further detail below).

In this embodiment, the module is pre-assembled from the frame and the fibre optic to allow easy installation on the vessel 10. The frame 20 is planar, but has sufficient flexibility and compliance to allow it to be curved around the outer surface of the vessel. In alternative embodiments, the frame may have an intrinsic curvature to match the shape of the vessel.

Ceramic insulating material (not shown) is placed between the fibre optic cable 21 and the frame 23 to insulate the fibre optic from the effects of the environment.

Figure 3:
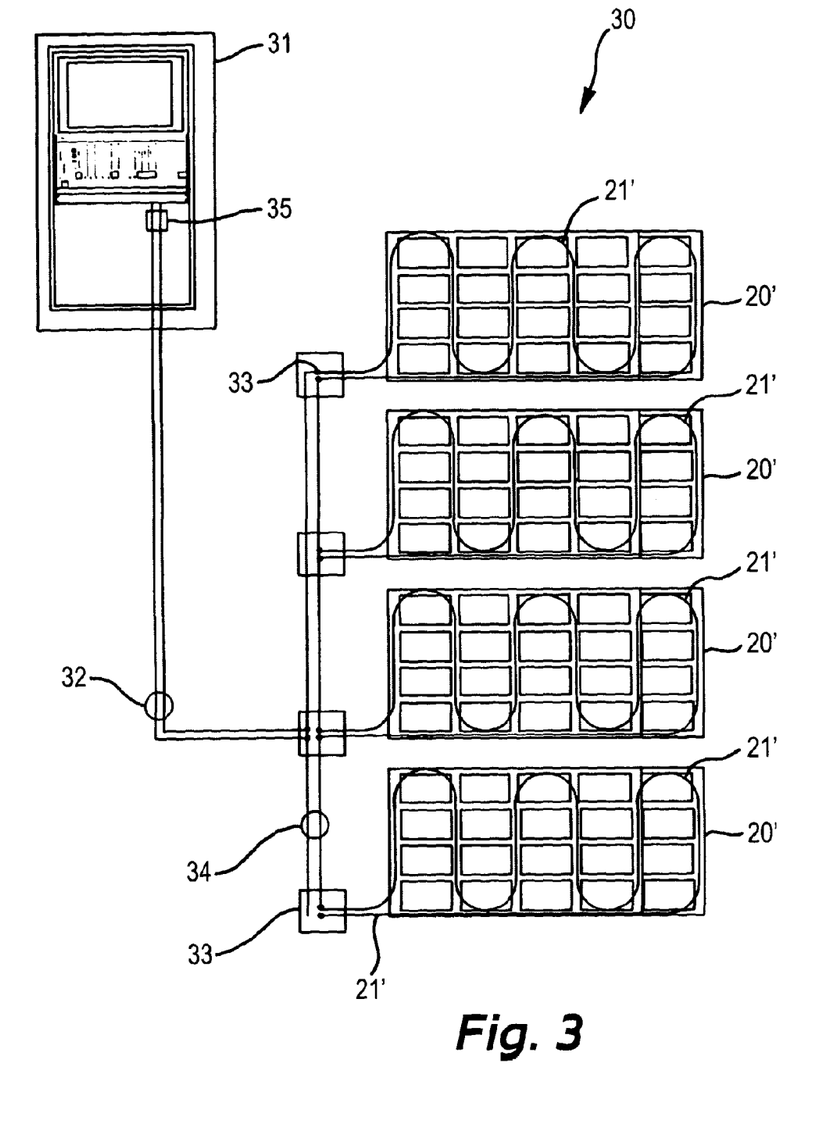
FIG. 3 is a schematic view of a fibre optic monitoring system according to an embodiment of the invention.

FIG. 3 shows schematically a fibre optic monitoring system 30 comprising multiple modules 20'. The modules 20' are similar to modules 20, and will be understood from FIG. 2 and the accompanying description. The module 20' differs from the module 20 in the layout of the frame and the orientation of the fibre optic length, but functions in the same way. The system 30 comprises multiple (in this case four) modules 20' which, each of which define a monitoring area. In use, the modules 20' are located against the surface of the vessel 10 to be sensitive to a condition of the vessel 10. The system 30 is configured as a Distributed Temperature Sensor (DTS) system for monitoring the temperature of the outer wall of the vessel 10, and the fibre optic lengths 21' are selected for high temperature operation. The system 30 comprises a DTS instrument 31 located remote from the vessel 10 in a control room (not shown). A surface cable 32 with a multiple fibre optic core is routed from the control room to the vessel 10. The surface cable 32 is selected to meet fire and safety standards.

The ends of the fibre optic lengths 21' are connected in series by splicing them together in a junction box 33 via interconnecting cable 34 to form a loop. The interconnecting cable 34 is protected by a metal tube (not shown) to provide additional protection during routine maintenance work. Access to both ends of the fibre optic lengths 21' is provided by splicing the two ends of the loop to two separate fibres in the surface cable 32.

An optical switch 35 is incorporated at the optical output of the DTS instrument 31 which enables the monitoring of the fibre loop from both ends. This has two advantages. The first advantage is that the temperature accuracy can be improved by combining the two measurements. The second advantage is that the whole length of the fibre can be monitored if there is a break in the fibre.

Although the system 30 is configured for monitoring one vessel 10, the system can be extended to monitor additional vessels. For example, the fibre optic lengths of additional modules may be spliced in series with the fibre optic lengths 21' to form a part of the loop. Alternatively, they may be routed separately back to the DTS instrument via additional fibres in the surface cable 32, used in conjunction with a multichannel optical multiplexer (not shown) to sequentially monitor the additional vessels.

Figure 4:
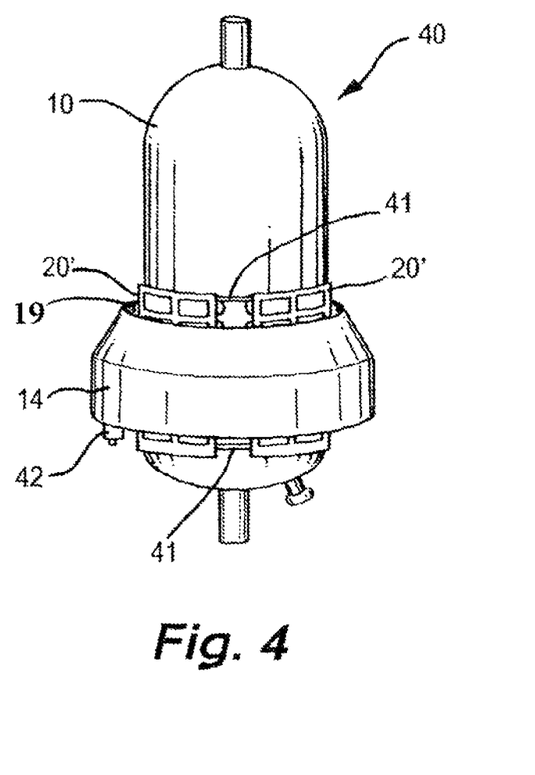
FIG. 4 is a perspective view of a fibre optic monitoring installation according to an embodiment of the invention.

FIG. 4 shows the system 30 in a fibre optic monitoring installation 40 on a vessel 10. The installation 40 comprises four modules 20 installed on the vessel 10, in the annular space 19 between the vessel 10 and the concrete support 14. The modules 20 are arranged to present their respective fibre optic lengths to the surface, such that they are sensitive to the temperature conditions of the vessel. Each module can be installed individually on the vessel to cover a monitoring area or zone. The modules 20 are connected together by connectors 41 and placed under tension to ensure good thermal conduct between the fibre and the vessel and accommodate thermal expansion and contraction of the vessel. Examples of installation methods are described in more detail below.

In use, the system monitors the surface of the vessel 10 to provide quantitative temperature data. The installation 40 also optionally comprises a visual and audible indicator 42 which is activated in response to the detection of an undesirable temperature condition. When a hotspot is detected an alarm signal is sent to the local indicator 42 via the surface cable to draw immediate attention to the detected condition. The surface cable may therefore be a hybrid electrical and optical cable. In an alternative embodiment the warning signal may be transmitted optically, which is advantageous if it is undesirable to provide electrical cables in the vicinity of the vessels.

Methods of forming the monitoring installation 40 will now be described. The frames allow convenient installation of the system on parts of the surface which are difficult to reach due to the geometry of the installation. However, it will be appreciated that the invention also has benefits when the modules are installed in accessible areas of the vessel, including ease of installation and removal. Furthermore, the invention allows the system to be installed and/or removed without interrupting the operation of the vessel.

Figure 5:
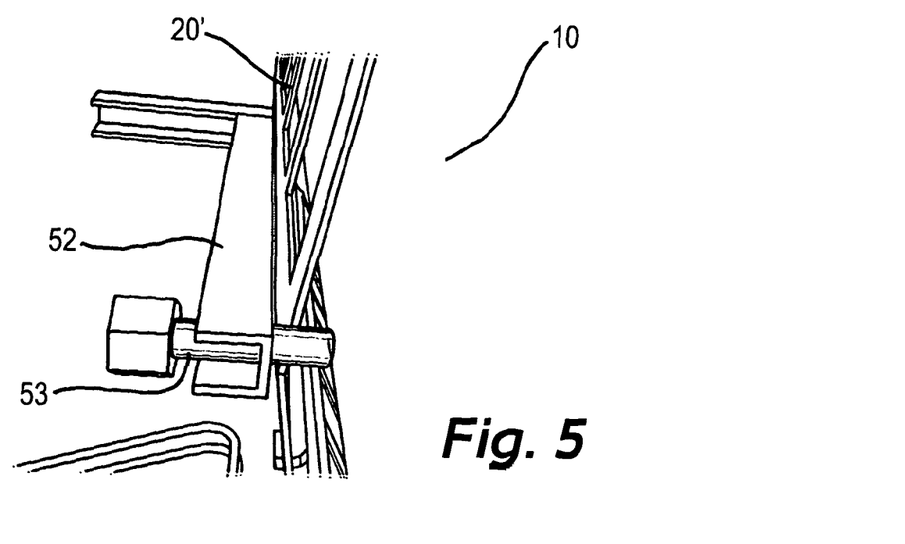
FIG. 5 shows an initial installation step according to an embodiment of the invention.

In the embodiment of FIG. 4, lower part of the vessel beneath the concrete support is more accessible from below than from above. The individual modules are pre-assembled, and are positioned against the surface of the vessel by raising the modules up into the annular space between the concrete support 14 and the vessel from below. FIG. 5 shows an initial stage of installation, in which a module 20' is vertically supported in the annulus by a bracket 52. The bracket 52 is an "L-shaped" bracket fitted to the concrete support (not shown in FIG. 5), and comprises a pin 53 which supports the module 20' vertically in the space. Additional modules are positioned against the surface of the vessel sequentially around the vessel, and supported vertically by similar brackets.

Figure 6A:
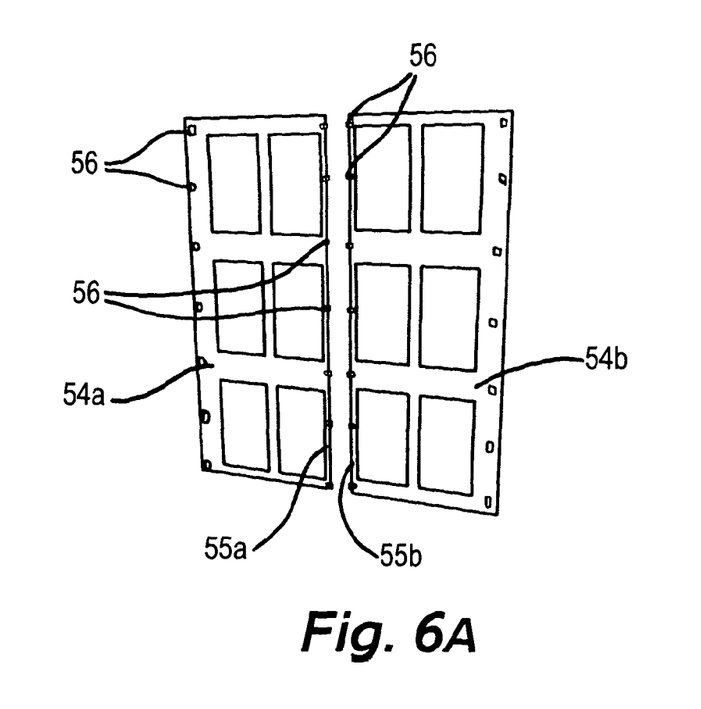
FIGS. 6A to 6C show schematically steps of an installation method according to an embodiment of the invention.
Figure 6B:
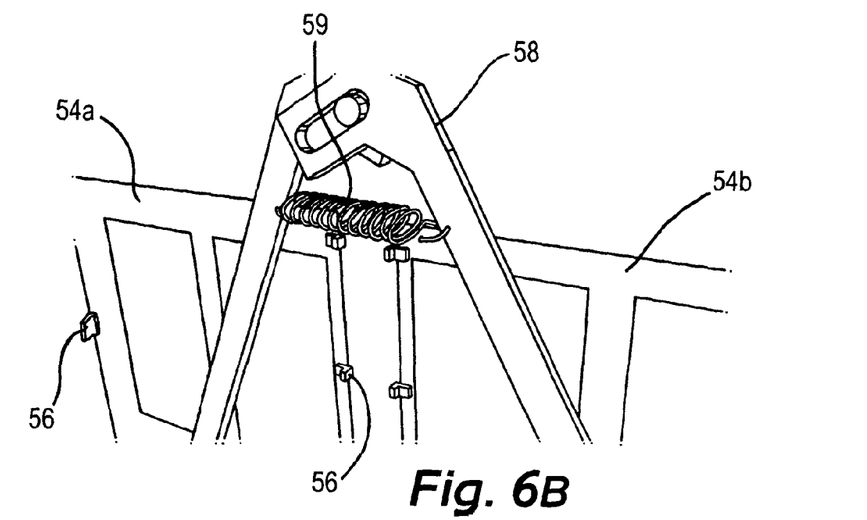
Figure 6C:
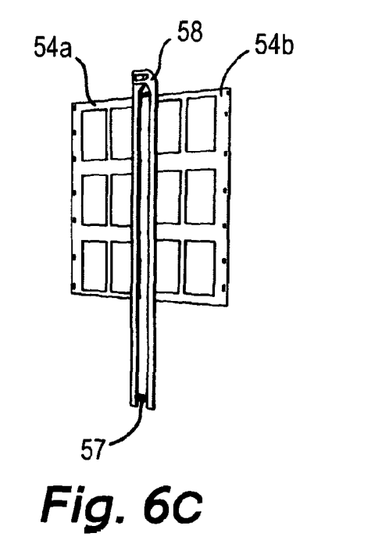

FIGS. 6A to 6C show schematically a mechanism by which the system is installed according to one embodiment. For clarity, these drawings show a pair of frames 54a, 54b which make up a pair of modules, with the fibre optic lengths omitted and outside of the installation 40. It will be appreciated that same mechanism may be used in the annular space between the vessel and the concrete support.

Each frame 54a, 54b comprises connector formations 56 along opposing adjacent edges 55a, 55b. The formations 56 are located along the edges and extend from the plane of the frames to form abutment surfaces. The formations are arranged in corresponding pairs which are designed to be brought together during installation. As most clearly shown in FIGS. 6B and 6C, a pivoting clamp 58 is located around the formations 56, opened against the force of a spring 59. The open ends of the clamp 58 are brought together to engage the abutment surfaces of the formations 56 and bring the edges 55a, 55b of the frames together, as shown in FIG. 6C. An additional spring 57 connects the lower ends of the clamp 58.

For the installation of the monitoring system 40, the method takes place inside the annular space 19 between the vessel and the concrete support 14. The frames are located in the annular space and vertically supported by the brackets 52. The clamp 58 is located in the annular space 19 and positioned around the formations 56. The ends of the clamp 56 are brought together to engage the abutment surfaces of the formations 56 and bring the edges 55a, 55b of the frames together, and an additional spring 57 connects the lower ends of the clamp 58. The attachment mechanism applies tension to the modules in the installation to maintain good physical contact between the fibre optic lengths and the vessel and therefore maintain sensitivity to the vessel condition. In addition, it allows the modules to be brought together from an access position located above or below the modules, enabling the modules to be assembled over areas which are difficult to reach such as behind structural elements.

Each of a plurality of modules may be brought together and attached in the manner described above. Alternatively, some of the modules may be mechanically fixed to one another with only one (or some) of the interfaces between adjacent modules having a tensioned connection.

Figure 7:
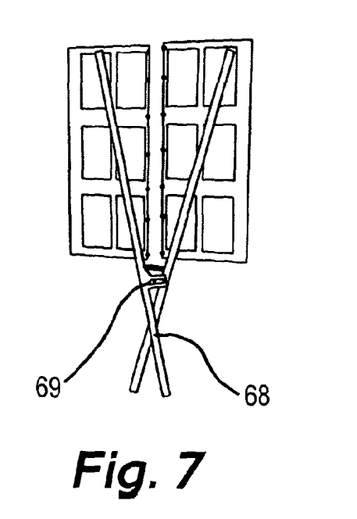
FIG. 7 shows schematically a step of an installation method according to an alternative embodiment of the invention.

Variations to the described embodiment are within the scope of the invention. In one alternative, the clamp is provided with hooks which engage with slots in the frames. In another, as shown in FIG. 7, the clamp 68 is a scissor-type clamp with a pivot 69 located part-way along its length. This arrangement operates similarly to the arrangement of FIGS. 6A to 6C, although it does not require the clamp to be located around the formations on the frames. Instead, the clamp 68 operated from below can be positioned on the outside of the formations on the frames from below (as shown in the drawing), and is not required to manipulated over the uppermost formations. This facilitates positioning of the clamp in narrow access areas, and the minimal extent of the clamp above the frames may allow them to be positioned higher up in a restricted space. It will be appreciated that this configuration can be inverted for operation from above.

Figure 8A:
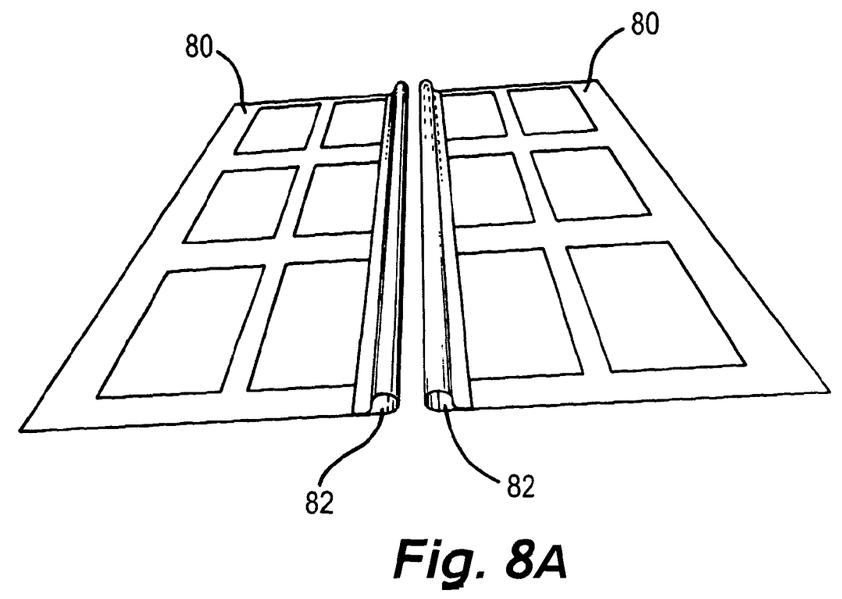
FIGS. 8A to 8B show schematically steps of an installation method according to an alternative embodiment of the invention.
Figure 8B:
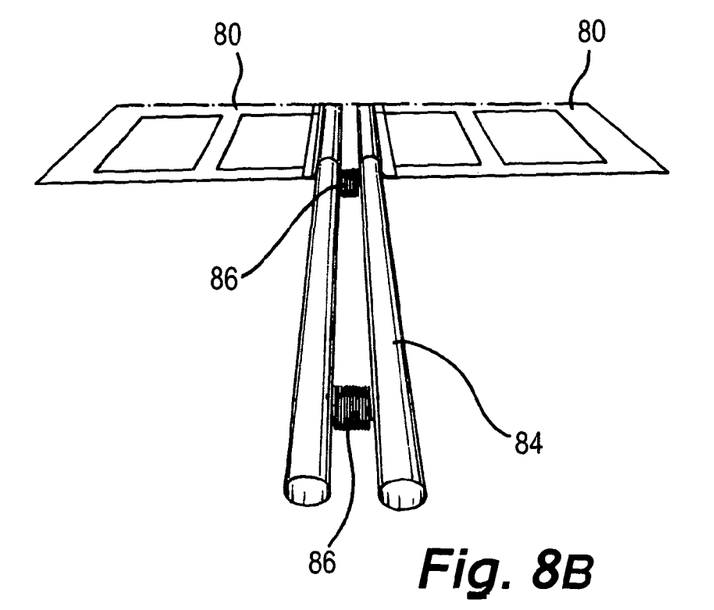

A further alternative embodiment is illustrated in FIGS. 8A and 8B. In this embodiment, the frames 80 are provided with channels 82 formed by bending the material of the frame. The channels are shaped to receive a rod clamp 84, which is inserted into the channels 82 to allow the frames to be positioned in relation to the vessel. After positioning of the panels, high strength springs 86 are installed around the rods to maintain the modules under sufficient tension to accommodate for thermal expansion of the vessel in operation.

Figure 9A:
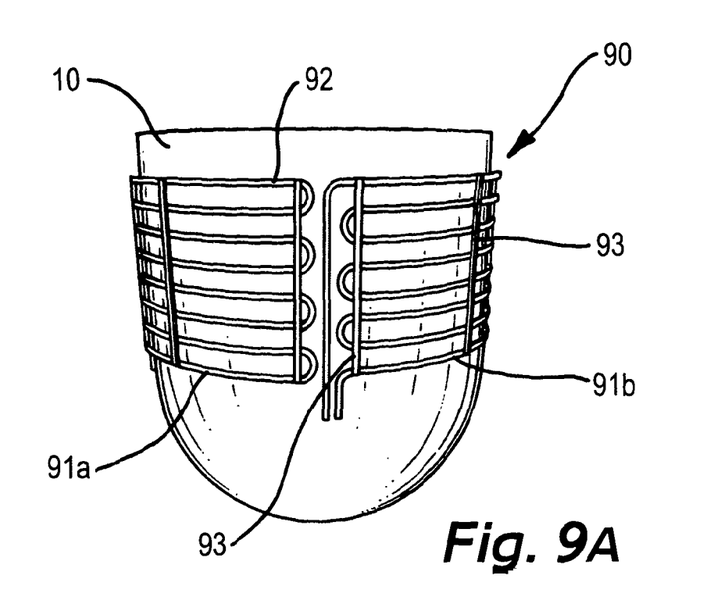
FIG. 9A is a perspective view of a fibre optic monitoring installation according to an alternative embodiment of the invention.
Figure 9B:
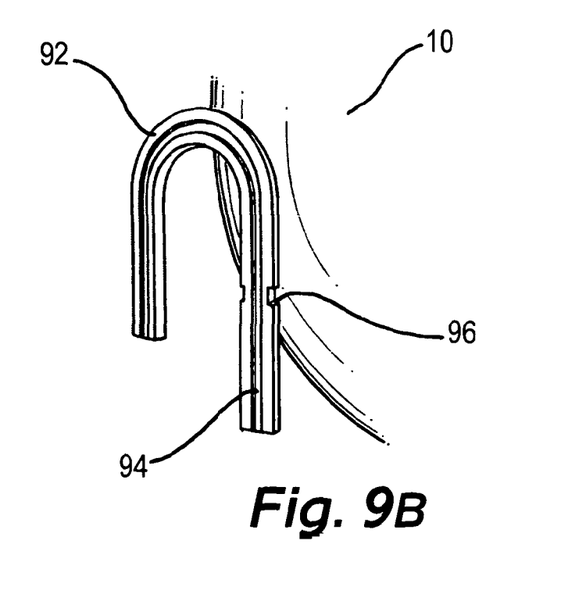
FIG. 9B is an enlarged view of the support structure of the embodiment of FIG. 9A.

FIGS. 9A and 9B show a fibre optic monitoring installation 90 according to another embodiment of the invention. FIG. 9A shows the system formed from modules 91a, 91b, located on the vessel. Each module comprises a custom-fabricated aluminium channel structure 92 welded to supports 93. The channel structure 92, most clearly shown in FIG. 9B, comprises a channel for receiving the fibre optic length 94. The depth of the channel is less than 50% of the cable diameter to ensure that sufficient fibre is upstanding from the channel to provide good contact with the vessel. The channel structure 92 is shaped to follow the curve of the surface of the vessel to which it is attached. This allows firm pressure to be applied over the entire surface using L-shaped brackets secured to the concrete support.

The fibre optic length is secured to the channel structure 92 using cable ties, which are held in place along the length of the channel by notches 96. In addition, ceramic insulating material (not shown) is placed between the fibre optic cable and the channel structure 92 to insulate the fibre optic from the effects of the environment.

Figure 10A:
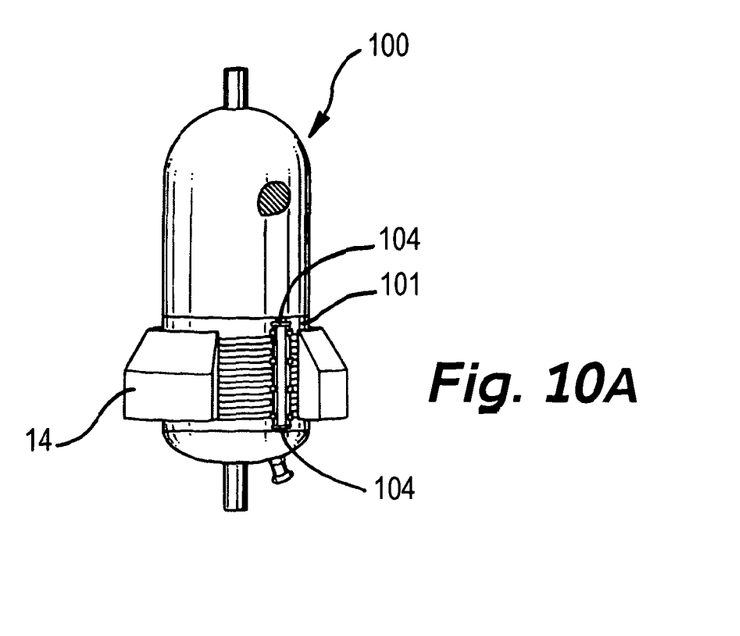
FIG. 10A is a perspective view of a fibre optic monitoring installation according to an alternative embodiment of the invention.
Figure 10B:
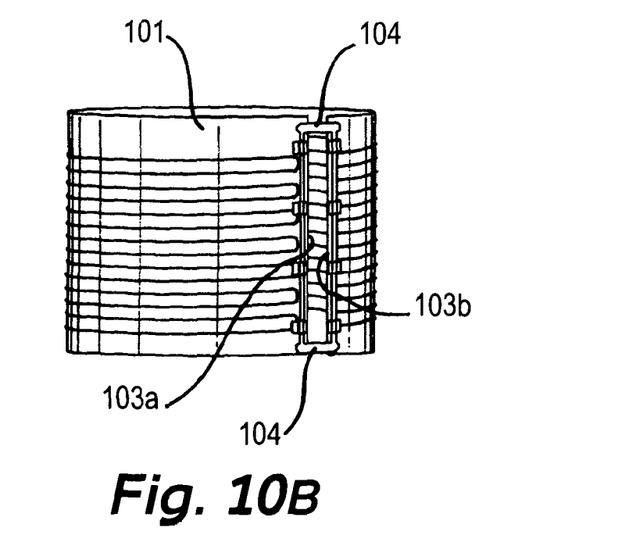
FIG. 10B is an enlarged view of the support structure of the embodiment of FIG. 10A.

FIGS. 10A and 10B show an alternative embodiment 100 of the invention, in which the support structure for the fibre optic cable is a flexible sleeve 101 of fibrous material. FIG. 10A shows the installation system 100, having a part of the concrete support 14 removed to show the sleeve 101 beneath. FIG. 10B shows the sleeve 101 and fibre optic assembly prior to installation.

The sleeve 101 is approximately 3 to 7 mm thick and supports the fibre optic length in a preformed orientation. The insulating material of the sleeve reduces the effect of ambient temperature on the monitoring operation, and also prevents conduction of heat from the vessel to the concrete support. The internal structure of the sleeve 101 is supported by a steel mesh (not shown). In order to allow installation behind the concrete collar, the blanket is fitted around the vessel by opening the sleeve at edges 103a, 103b and placing the sleeve around the vessel. The sleeve is positioned vertically on the vessel and the edges 103a, 103b are attached to one another at points above and below the concrete support using by spring-loaded attachment mechanisms 104. The mechanisms tension the sleeve to maintain close contact between the vessel and the fibre optic lengths.

Figures 11A, 11B, 11C:
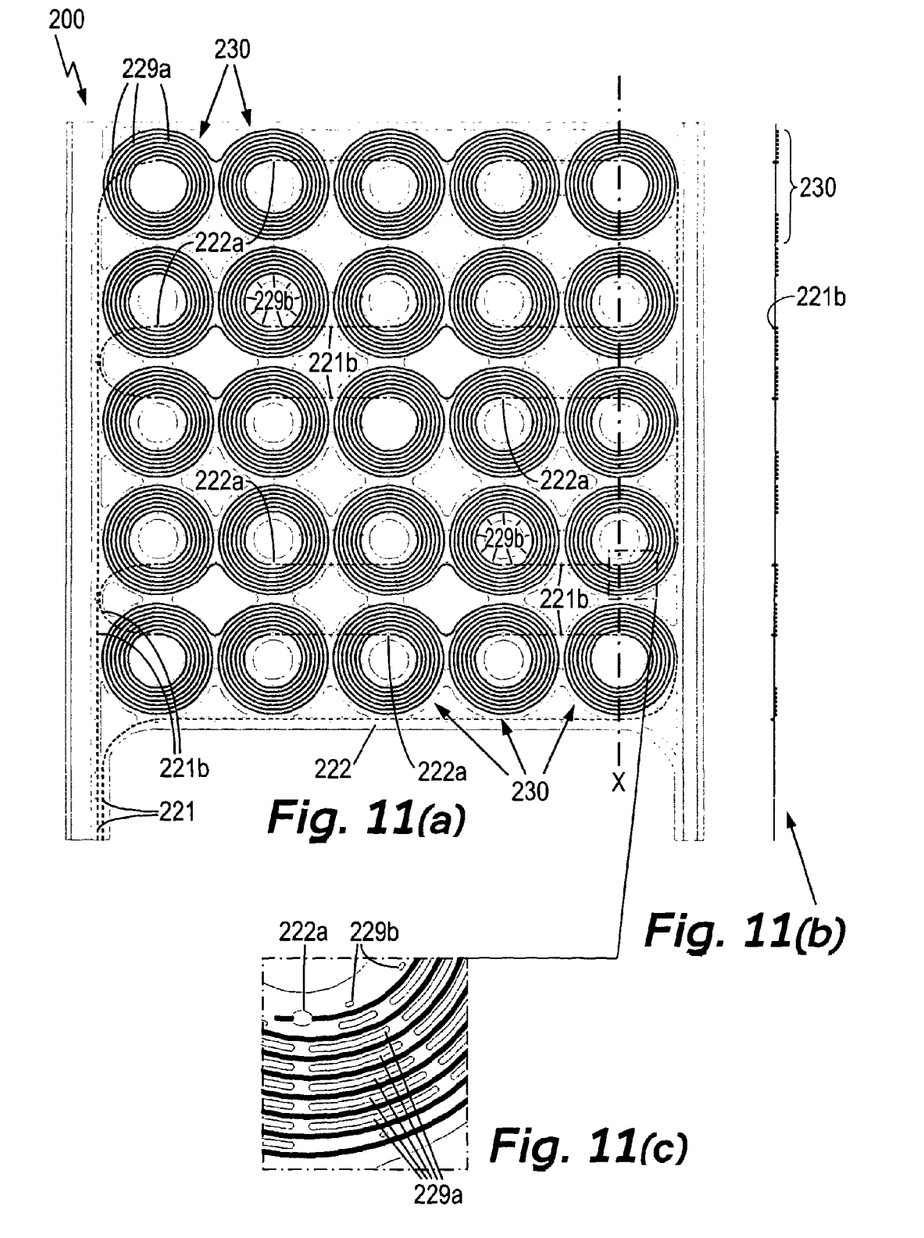
FIG. 11 is a side view of a module according to an alternative embodiment of the invention.

In FIG. 11(a), an alternative module 200 is shown in which a very high density of fibre 221 is accommodated on a panel 222. The dashed portions 221b of the fibre 221 indicate where the fibre 221 is passed behind the panel 222 (via apertures 222a) to avoid having the fibre 221 physically cross itself. In this way, a series of dense spirals 230 is able to be provided without risking the fibre 221 being bent, crushed or otherwise damaged when, for example, the module 200 is pressed onto a vessel to be monitored. Of course, a number of alternative patterns may be achieved in this way. FIG. 11(b) shows a cross-section through line X illustrating the location of the fibre 221 on opposite sides of the panel when in one of the spirals 230, or behind 221b the panel 222 between spirals 230. FIG. 11(c) shows an enlarged view of a portion of one of said spirals 230.

In this particular embodiment, the panel 222 may be pre-shaped to correspond, for example, to the shape of a vessel to be monitored such that it may be installed directly. Of course, similarly to previously described embodiments, the panel 222 may be planar and able to conform to the shape of a vessel to be monitored as it is installed.

The front face of the panel 222 (i.e. that facing out of the drawing in FIG. 11(a) and to the right of the drawing in FIG. 11(b) and that which is applied to the vessel surface) is provided with a number of fibre guide portions, such as protruding ribs 229a, which define and arrange the fibre 221 in a spiral path and a number of attachment points 229b which hold the fibre 221 in place. The attachment points 229b shown herein are short panel pass-throughs corresponding to the spiral path defined by the fibre guide portions 229a and ensure the fibre 221 is held in this configuration. Alternative attachment points may take the form of clips, studs, loops or other attachment means that would be apparent to the skilled person as suitable for this purpose.

The fibre guide portions 229a are shown in a concentric or quasi-concentric arrangement, and the attachment points 229b in a radial arrangement, however the skilled person will readily understand that a number of variations on and of these arrangements can be employed to effect and maintain a spiral (or other shaped) fibre configuration.

The provision of a series of dense spirals 230 also provides significant measurement and processing enhancements. For example, when a DTS is employed (such as described in relation to FIG. 3) the measurement density is vastly increased over previously described module embodiments, and the spirals themselves can be treated in processing as an array of virtual point sensors. Similarly, a number of said modules 200 may be connected to one another for further enhanced measuring and monitoring capability.

The invention provides a fibre optic monitoring installation and method of installation for an article such as a catalytic reforming process vessel. The installation comprises a fibre optic support structure arranged to support a fibre optic length in a predetermined orientation, which corresponds to a part of a surface of the article. The fibre optic support structure is located in relation to article such that in use the fibre optic length is sensitive to a condition (such as a temperature) of the surface of the article. Fibre optic instrumentation is coupled to the fibre optic length. Preferably the installation is a modular system of modules which allow convenient fitting of the fibre optic lengths to the article.

The present invention in its various aspects and embodiments offers a number of advantages over previously proposed fibre optic monitoring installations, apparatus and methods. Firstly, the invention allows convenient and fast installation and removal of fibre optic lengths by providing a support structure which orientates the fibre optic in a desired pattern. The invention enables fibre optic installation and/or removal while an article is in operation in an industrial process, and protects the fibre optic from mechanical damage.

The invention allows installation of fibre optic lengths over difficult-to-reach surfaces of an article to be monitored, such as parts of catalytic reforming process vessels which are obscured by structural elements. The installation methods and apparatus allow tensioning of the monitoring apparatus to maintain good contact between the fibre optic and the vessel (and therefore good sensitivity). Modular systems of embodiments of the invention facilitate removal and replacement of parts of the monitoring system without interfering with the operation and/or monitoring of other parts of the article.

Various modifications may be made within the scope of the invention as herein intended, and embodiments of the invention may include combinations of features other than those expressly disclosed herein. In particular it will be appreciated that many features of the various embodiments of the invention can be interchanged with one another or used in combination in alternative installation designs.

The invention claimed is:

1. A fibre optic monitoring installation comprising:
   an article having an outer surface to be monitored;
   a fibre optic support structure arranged to support a fibre optic length, wherein the support structure defines a monitoring area which corresponds to a part of a surface of the article, and the fibre optic length is arranged in a predetermined pattern or orientation on the support structure such that the fibre optic length is located over the monitoring area defined by the support structure;
   means for locating the fibre optic support structure in relation to the article such that, in use, the fibre optic length is sensitive to a condition of the surface of the article; and
   fibre optic instrumentation coupled to the fibre optic length,
      wherein the support structure comprises a panel comprising a plurality of guide portions on a surface thereof, the guide portions comprising a plurality of protruding ribs configured so as to arrange the fibre optic length in the predetermined orientation.

2. The fibre optic monitoring installation according to claim 1, wherein the guide portions are arranged to arrange the fibre optic length in a plurality of fibre spiral patterns.

3. The fibre optic monitoring installation according to claim 1, wherein the panel comprises a plurality of apertures to allow the fibre to pass to another surface of the panel.

4. A fibre optic monitoring installation comprising:
   an article having an outer surface to be monitored;
   a fibre optic support structure arranged to support a fibre optic length, wherein the support structure defines a monitoring area which corresponds to a part of a surface of the article, and the fibre optic length is arranged in a predetermined pattern or orientation over the monitoring area defined by the support structure;
   means for locating the fibre optic support structure in relation to the article such that, in use, the fibre optic length is sensitive to a condition of the surface of the article;
   fibre optic instrumentation coupled to the fibre optic length;
   a plurality of modules, each module comprising a fibre optic support structure and a fibre optic length; and
   one or more clamping assemblies configured to locate the plurality of modules such that their respective fibre optic lengths are presented to the surface of the articles, the clamping assembly comprising a pivoting clamp assembly, configured to engage with formations on frames of the modules.

5. The fibre optic monitoring installation according to claim 4, wherein the pivoting clamp assembly is operable to engage with formations on the frames to bring adjacent frames together, and/or to impart tension to the installation.

* * * * *